United States Patent
Kaku (10) Patent No.: US 9,072,453 B2
(45) Date of Patent: Jul. 7, 2015

(54) ENDOSCOPE APPARATUS

(75) Inventor: Toshihiko Kaku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 221 days.

(21) Appl. No.: 13/359,440

(22) Filed: Jan. 26, 2012

(65) Prior Publication Data

US 2012/0220824 A1 Aug. 30, 2012

(30) Foreign Application Priority Data

Feb. 24, 2011 (JP) ................. 2011-038269

(51) Int. Cl.
| | |
|---|---|
| A61B 1/04 | (2006.01) |
| A61B 1/06 | (2006.01) |
| A61B 1/00 | (2006.01) |
| G06T 5/00 | (2006.01) |
| A61B 1/05 | (2006.01) |

(52) U.S. Cl.
CPC ............ A61B 1/0638 (2013.01); A61B 1/0669 (2013.01); A61B 1/00009 (2013.01); A61B 1/05 (2013.01); G06T 5/009 (2013.01); G06T 2207/10068 (2013.01); G06T 2207/10152 (2013.01); A61B 1/063 (2013.01); A61B 1/0653 (2013.01)

(58) Field of Classification Search
CPC ........... A61B 1/00004; A61B 1/00009; A61B 1/0638; A61B 1/0669; H04N 5/325
USPC ............ 600/103, 109, 118, 160, 178; 348/65, 348/68, 74
See application file for complete search history.

(56) References Cited

U.S. PATENT DOCUMENTS

| | | | | |
|---|---|---|---|---|
| 5,204,919 | A * | 4/1993 | Murakami | 382/263 |
| 6,905,462 | B1 * | 6/2005 | Homma et al. | 600/176 |
| 7,418,132 | B2 * | 8/2008 | Hoshuyama | 382/167 |
| 7,892,169 | B2 | 2/2011 | Gono et al. | |
| 2002/0163670 | A1 * | 11/2002 | Takahira | 358/3.27 |
| 2003/0176768 | A1 | 9/2003 | Gono et al. | |
| 2008/0281154 | A1 | 11/2008 | Gono et al. | |
| 2008/0294105 | A1 | 11/2008 | Gono et al. | |
| 2011/0034770 | A1 | 2/2011 | Endo et al. | |
| 2012/0063662 | A1 * | 3/2012 | Kwon et al. | 382/132 |

FOREIGN PATENT DOCUMENTS

| | | |
|---|---|---|
| EP | 1 992 270 A1 | 11/2008 |
| JP | 06-339458 A | 12/1994 |
| JP | 10-290779 A | 11/1998 |

(Continued)

OTHER PUBLICATIONS

Japanese Office Action dated Jan. 15, 2013 and partial english translation thereof.

(Continued)

*Primary Examiner* — John P Leubecker
(74) *Attorney, Agent, or Firm* — McGinn IP Law Group, PLLC (57) ABSTRACT

An endoscope apparatus includes a light source unit, an imaging element, a density calculating section, and an image processing section, wherein the image processing section changes frequency processing conditions with respect to the captured image such that the detection and enhancement degree of the structure and components of the living body in the subject are changed according to at least the density of each pixel of the captured image.

5 Claims, 9 Drawing Sheets

(56) References Cited

FOREIGN PATENT DOCUMENTS

| JP | 2000-148987 | A | 5/2000 |
| JP | 3559755 | B2 | 9/2004 |
| JP | 3607857 | B2 | 1/2005 |
| JP | 2011-36361 | A | 2/2011 |

OTHER PUBLICATIONS

Partial Eurpean Search Report dated Jan. 17, 2013.
Extended Eurpean Search Report dated Mar. 25, 2013.

* cited by examiner

ENDOSCOPE APPARATUS

BACKGROUND OF THE INVENTION

The present invention relates to an endoscope apparatus that can perform special light observation using specific narrowband light in addition to normal light observation using broadband light, such as white illumination light.

In recent years, an endoscope apparatus that can perform so-called special light observation that irradiates specific narrow wavelength band light (narrowband light) onto a mucosal tissue of a living body and acquires tissue information at a desired depth of the body tissue has been utilized. This type of endoscope apparatus can simply visualize living body information that is not acquired in normal observation images, such as enhancement of the surface layer fine structure of a new blood vessel generated in a mucosal layer or a submucosal layer, and a lesional part. For example, when an observation target is a cancerous lesional part, the state of fine blood vessels or fine structure of a tissue surface layer can be observed in more detail if blue (B) narrowband light is irradiated on a mucosal tissue. Therefore, the lesional part can be more accurately diagnosed.

In the special light observation, in image processing, a G image signal is allocated to B image data, a B image signal is allocated to G image data and B image data, and a pseudo-color image including 3ch color image data is generated, and is displayed on a monitor or the like.

As a result, it is known that, since the pseudo-color image displayed on the monitor or the like includes a number of B image signals (B narrowband data) mainly including information on a surface layer tissue, the state of the fine blood vessels and fine structure of the surface layer tissue is expressed in more detail, and the fine blood vessels and fine structure of the surface layer tissue may be easily observed (JP 3559755 B and JP 3607857 B).

SUMMARY OF THE INVENTION

Even in the normal light observation as well as the special light observation as described above, when the distance between a diseased tissue and the irradiation position of illumination light is small, the fine blood vessels and fine structure of the tissue surface layer, which are bright and clearly visible, can be captured. However, there is a problem in that the quantity of light becomes insufficient as the distance becomes longer, whereby it is dark and visibility is hindered.

Additionally, if the distance between the diseased tissue and the irradiation position of illumination light changes as mentioned above, and the magnifying power of a subject tissue is changed, whereby the pixel size of blood vessels projected on an imaging element changes, there is a problem in that it becomes difficult to recognize the surface layer fine blood vessels.

Moreover, when an imaging position is distant, a region where surface layer fine blood vessels are densely present, which is called a brownish region, and individual lumps of the blood vessels become an observation target instead of the individual surface layer fine blood vessels, and the image processing to be applied to a captured image differs. However, since the switching of these kinds of image processing is generally manually performed, there is a problem in that suitable image enhancement is not necessarily performed.

Additionally, in the endoscope observation, when the distal end of the endoscope is not perpendicular to a subject tissue, such as the alimentary mucosa, or when observation is performed while the endoscope is inserted into and extracted from an alimentary canal, different distances are present on the same captured image. As a result, ever, if suitable image processing (for example, image enhancement) is performed in a portion on the captured image, suitable image processing is not performed in the other most portion.

In this case, observation is obliged to be performed while changing the distance, or observation is obliged to be performed while changing the processing to be applied to a captured image, and thus, observation of the captured image requires substantial time and effort.

An object of the invention is to provide an endoscope apparatus that does not need to intentionally adjust the irradiation light quantity, a light emission ratio, and image processing of special light and white illumination light while a manipulator observes a captured image, in both of the normal light observation and the special light observation, can perform image processing suitable for the captured image according to a distance even if portions that have different distances from the distal end of an endoscope from each other are present on the same captured image, and can obtain a captured image that is optimal and bright in relation to the observation of the structure and components of living bodies, such as surface layer fine blood vessels.

In order to achieve the above-mentioned objects, the invention provides an endoscope apparatus comprising:

a light source unit that is capable of adjusting the quantity of light and irradiates illumination light to a subject;

an imaging element that captures a capturing image by return light from a living body that is the subject in the illumination light and outputs a captured image signal;

a density calculating section that calculates the density of each pixel of the captured image on the basis of the captured image signal; and an image processing section that performs a predetermined image processing on the captured image, wherein the image processing section changes frequency processing conditions with respect to the captured image such that the detection and enhancement degree of the structure and components of the living body in the subject are changed according to at least the density of each pixel of the captured image.

Further, preferably, the image processing section includes a frequency band enhancing section that enhances a predetermined frequency band, and the frequency band enhancing section changes the frequency band to be enhanced according to the density of each pixel of the captured image.

Further, preferably, the frequency band enhancing section weakens the enhancement degree as the density becomes large, and strengthens the enhancement degree as the density becomes small.

Further, preferably, the frequency band enhancing section changes the bandwidth of the frequency band to be enhanced according to the density of each pixel of the captured image.

Further, preferably, the frequency band enhancing section changes the center of the frequency band to be enhanced, according to the density of each pixel of the captured image.

The present invention also provides an endoscope apparatus comprising:

a light source unit that is capable of adjusting the quantity of light and irradiates illumination light to a subject;

an imaging element that captures a capturing image by return light from a living body that is the subject in the illumination light and outputs a captured image signal;

a density calculating section that calculates the density of each pixel of the captured image on the basis of the captured image signal;

a light quantity calculating section that calculates light quantity information including the light quantity of the illumination light, and the light quantity of the return light obtained from the captured image signal of a predetermined portion of the captured image; and an image processing section that performs a predetermined image processing on the captured image, wherein the image processing section changes frequency processing conditions with respect to the captured image such that the detection and enhancement degree of the structure and components of the living body in the subject are changed according to the density of each pixel of the captured image and the light quantity information.

Further, preferably, the image processing section includes a distance estimating section, and the distance estimating section estimates the distance of each pixel of the captured image on the basis of the density of each pixel on the captured image and the light quantity information, and changes the frequency processing conditions with respect to the captured image according to the distance of each pixel of the captured image.

Further, preferably, the image processing section includes a frequency band enhancing section that enhances a predetermined frequency band, and the frequency band enhancing section changes the frequency band to be enhanced according to the distance of each pixel of the captured image.

The present invention also provides an endoscope apparatus further comprising a low-frequency component extracting section that extracts a low-frequency component of the captured image from the captured image signal to generate a low-frequency captured image, and outputs a low-frequency captured image signal, wherein the low-frequency captured image signal is used instead of the captured image signal in the density calculating section.

Further, preferably, wherein the light source unit includes:

a first light source section that emits broadband light having a wide wavelength band including a visible region, a second light source section that emits narrowband light having a wavelength bandwidth narrowbanded according to the spectral characteristics of the structure and components of the living body used as the subject, and a light source control section that controls light emission, irradiation light quantity, and, a light quantity ratio from the first light source section and the second light source section.

According to the endoscope apparatus of the invention, the density information of each pixel of a captured image is calculated, and the frequency processing conditions are changed on the basis of the density information. Thus, for example, even in a case where a lesional part is enlarged or imaging is performed from a near position and surface layer fine blood vessels are observed, a case where a lesional part is captured from a far position, and a brownish region, where surface layer fine blood vessels are densely present is observed, and a case where both a portion captured from a near position and a portion captured from a far position are mixed in one captured image, it is not necessary for the manipulator to intentionally adjust or change the light emission conditions of the light sources and the frequency processing conditions of the captured image while observing the captured image. Additionally, even in the case of special light observation of a lesional part, surface layer fine blood vessels, or the like as well as in the case of the normal light observation, an optimal and bright captured image can be obtained.

DETAILED DESCRIPTION OF THE INVENTION

An endoscope apparatus related to the invention will be described below in detail on the basis of preferred embodiments shown in the accompanying drawings.

Figure 1:
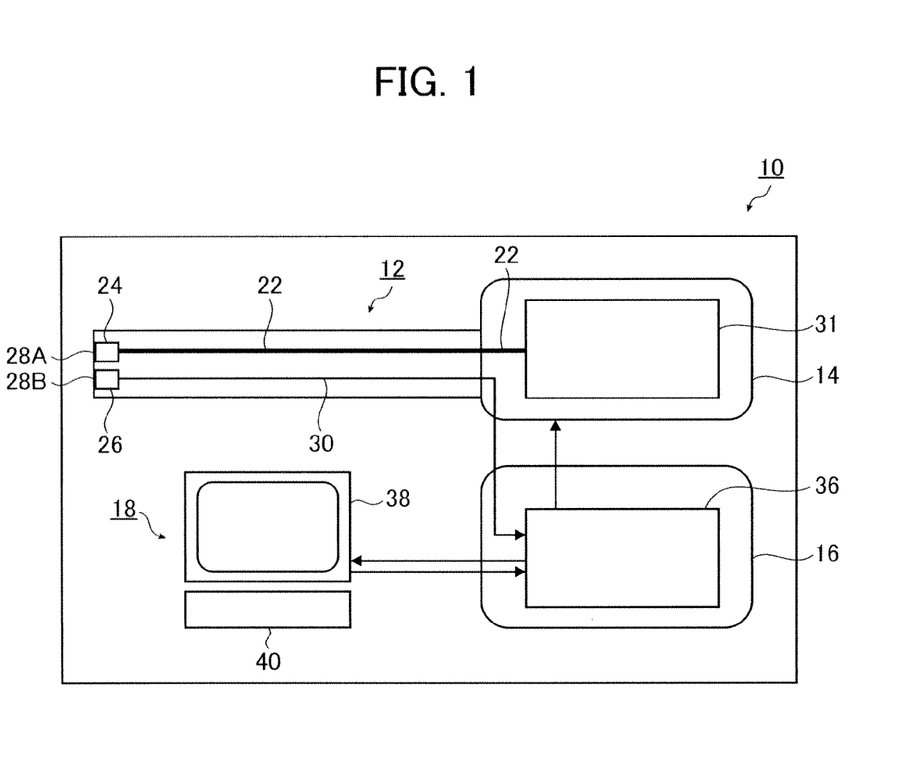
FIG. 1 is a block diagram schematically showing one example of the overall configuration of an endoscope apparatus of the invention.
Figure 2:
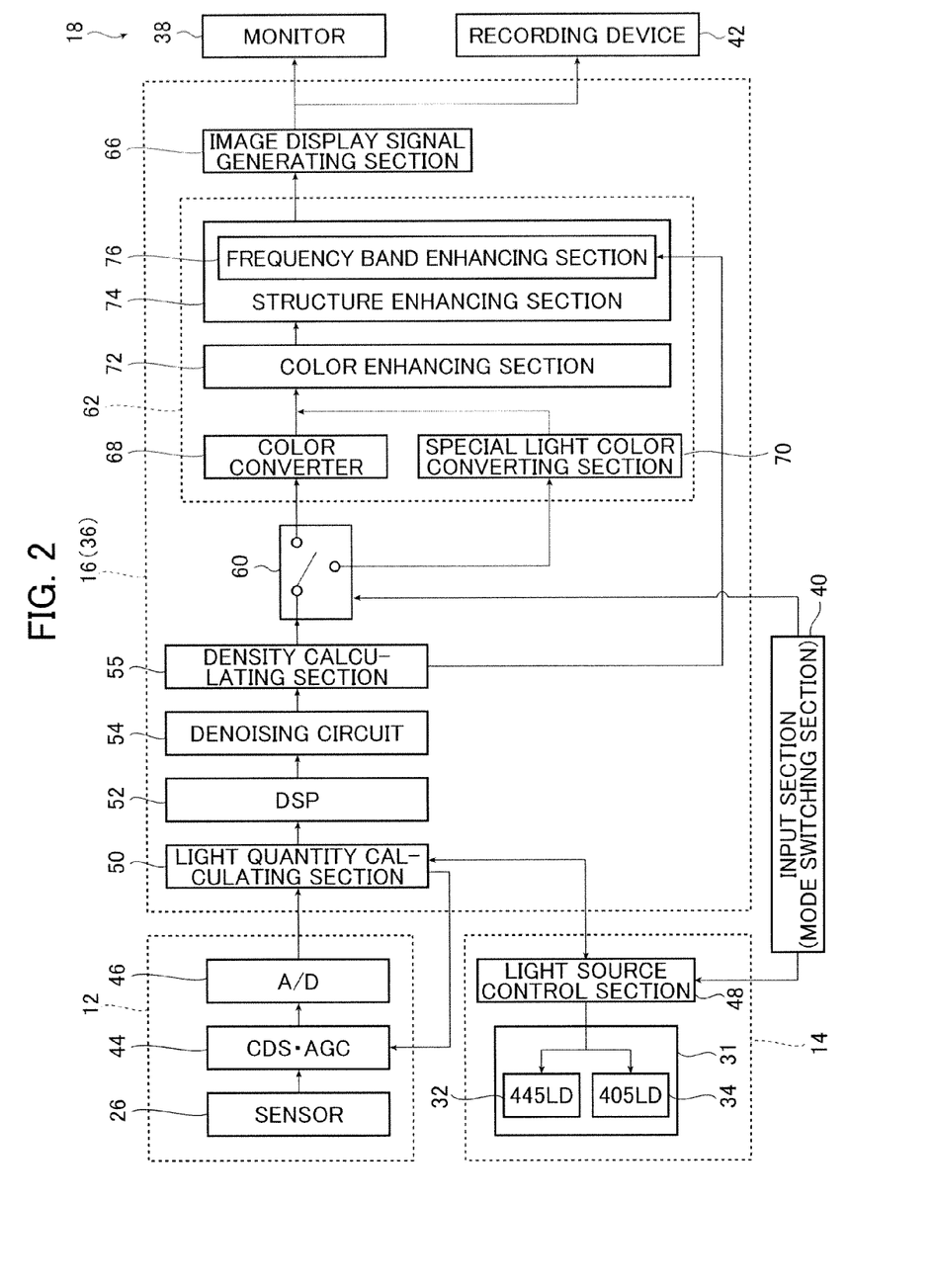
FIG. 2 is a block diagram showing signal processing systems of respective sections including the detailed configuration of the first embodiment of the endoscope apparatus shown in FIG. 1.

FIG. 1 is a block diagram schematically showing one example of the overall configuration of the endoscope apparatus of the invention, and FIG. 2 is a block diagram showing signal processing systems of respective sections including the detailed configuration of a first embodiment of processors of the endoscope apparatus of the invention.

As shown in FIG. 1, the endoscope apparatus 10 of the invention has an endoscope 12, a light source device (constitutes the light source unit of the invention along with a fluorescent body 24 to be described below) 14, a processor 16, and an input and output section 18. Here, the light source device 14 and the processor 16 constitute a control device of the endoscope 12, and the endoscope 12 is optically connected to the light source device 14, and is electrically connected to the processor 16. Additionally, the processor 16 is electrically connected to the input and output section 18. The input/output section 16 has a display section (monitor) 38 that displays image information or the like as output, a recording device 42 (refer to FIG. 2) that cutouts image information or the like, and an input section (mode switching section) 40 that functions as a UI (user interface) that receives input operations, such as mode switching to a normal light mode, a special light mode, or the like, and function settings.

The endoscope 12 is an electronic endoscope that has an illumination optical system that emits illumination light from the distal end thereof, and an imaging optical system that images a region to be observed. In addition, although not shown, the endoscope 12 includes an endoscope insertion part inserted into a subject, a manipulation part that performs curving manipulation of the distal end of the endoscope insertion cart, and manipulation for observation, and connector parts that detachably connect the endoscope 12 to the light source device 14 and the processor 16 of the control device. Moreover, although not shown, various channels, such as a forceps channel that allows a treatment tool or the like for tissue sampling to be inserted thereinto, and air supply and water supply channels, are provided inside the manipulation part and the endoscope insertion part.

As shown in FIG. 1, a fluorescent body 24, which constitutes the illumination optical system and a white light source, is provided in an irradiation port 28A that emits a region to be observed with light, at the distal end portion of the endoscope 12. An imaging element (sensor) 26, which constitutes the imaging optical system, such as a CCD (Charge Coupled Device) image sensor or a CMOS (Complementary Metal-Oxide Semiconductor) image sensor that acquires the image information of a region to be observed, is arranged at a light-receiving part 28B adjacent to the irradiation pert 28A. Additionally, a cover glass or a lens (not shown) that constitutes the illumination optical system is arranged at the irradiation port 29A of the endoscope 12, a cover glass or a lens (not shown) that constitutes the imaging optical system is arranged at the light-receiving part 28B, and an objective lens unit (not shown) that constitutes the imaging optical system is arranged at a light-receiving surface of the imaging element 26 of the light-receiving part 28B.

The endoscope insertion part is made curvable by the manipulation of the manipulation part, can be curved in arbitrary directions and at arbitrary angles according to the parts of a subject in which the endoscope 12 is used, and can direct the irradiation port 28A and the light-receiving part 283, that is, the observation direction of the imaging element 26, to a desired observation part.

In addition, although it is preferable that the imaging element 26 be a color imaging sensor or a complementary-color sensor including a color filter (for example, an RGB color filter or a complementary-color filter) in a light-receiving region, the RGB color imaging sensor is mere preferable.

Since the essence of the invention is not affected whether the invention is normal light observation or special light observation, it is not necessary to particularly limit the light source as long as adjustment of the irradiation light quantity is possible. In addition, the light source device 14 shown in FIG. 2 (FIGS. 9 and 11 to be described below are also the same) has a blue laser beam source (445LD) 32 with a central wavelength of 445 nm to be used as a white light source, and a blue-violet laser beam source (405LD) 34 with a central wavelength of 405 nm to be used as a special light source in the special light mode as a light emission source 31. Hence, it is possible to radiate both the special light and the normal light, in cooperation with the fluorescent body 24 to be described below.

The 445LD 32 constitutes a first light source section of the invention, and the 405LD 34 constitute a second light source section of the invention. In addition, since the blue-violet laser beam with a central wavelength of 405 nm from the 405LD 34 is narrowband light with a wavelength bandwidth that is narrowbanded according to the spectral characteristics of the structure or components of a living body, preferably, in conformity with the characteristics, the detectability of the structure or components of the living body is excellent.

The light emission from the 445LD 32 and the 405LD 34 is individually controlled by the light source control section 48 (refer to FIG. 2), and the light emission conditions of the 445LD 32 and the 405LD 34, that is, the light quantity ratio (light emission ratio) of the emitted light of the 445LD 32 and the emitted light of the 405LD 34 can be freely changed.

A broad area type InGaN-based laser diode can be used for the 445LD 32 and the 405LD 34, and an InGaNAs-based laser diode or a GaNAs-based laser diode can also be used. Additionally, the above light sources may be configured using light emitters, such as a light-emitting diode.

The laser beams irradiated from the 445LD 32 and the 405LD 34 are input to optical fibers 22, respectively, by condensing lenses (not shown), and are transmitted to a connector part via a multiplexer (not shown). In addition, the invention is not limited thereto, and may have a configuration in which the laser beams from the respective light sources 32 and 34 are respectively delivered directly to the connector part without using the multiplexer.

A blue laser beam with a central wavelength of 445 nm and a blue-violet laser beam with a central wavelength of 405 nm are multiplexed, and a laser beam transmitted to the connector part is propagated to a distal end portion of the endoscope 12 by the optical fibers 22 that constitute the illumination optical system, respectively. Then, the blue laser beam excites the fluorescent body 24 arranged at light irradiation ends of the optical fibers 22, at the distal end of the endoscope 12, thereby making the fluorescent body emit fluorescent light. Additionally, a portion of the blue laser beam transmits through the fluorescent body 24 as it is. The blue-violet laser beam transmits through the fluorescent body 24, whole hardly exciting the fluorescent body, and becomes illumination light (so-called narrowband light; with a narrowband wavelength.

The optical fiber 22 is a multimode fiber, and a fine-diameter fiber cable whose core diameter is 105 μm, cladding diameter is 125 nm, and for which a diameter including a protective layer serving as an outer skin is φ0.3 to 0.5 mm can be used as an example.

The fluorescent body 24 is configured so as to include a plurality of kinds of fluorescent bodies (for example, fluorescent bodies, such as a YAG-based fluorescent body or BAM ($BaMgAl_{10}O_{17}$)) that absorbs a portion of the blue laser beam, and is excited in green and yellow to emit light (emit fluorescent light). Thereby, green and yellow florescent light having the blue laser beam as excitation light, and the blue laser beam that is transmitted through the fluorescent body 24 without being absorbed thereby are combined, and become white (pseudo-white) illumination light. If the semiconductor light-emitting element is used as an excitation light source as the present embodiment, high-intensity white light can be obtained at high luminous efficiency, the intensity of the white light can be easily adjusted, and changes in color temperature and chromaticity of the white light can be suppressed to be low.

The fluorescent body 24 can prevent the superposition of noise which becomes an obstacle to imaging or the occurrence of flickering when a moving image display is performed, due to a speckle caused by the coherency of a laser beam. Additionally, the fluorescent body 24 is preferably consisted of a fluorescent material and a filler material, and the grain sizes of the fluorescent material and of the filler material are determined such that 24 has a small absorption and large scattering of infrared light in consideration of the refractive index difference between the fluorescent material and a fixing/solidifying resin working as the filler material. Thereby, a scattering effect is enhanced without reducing light intensity with respect to red light or infrared light, and optical loss becomes small.

Figure 3:
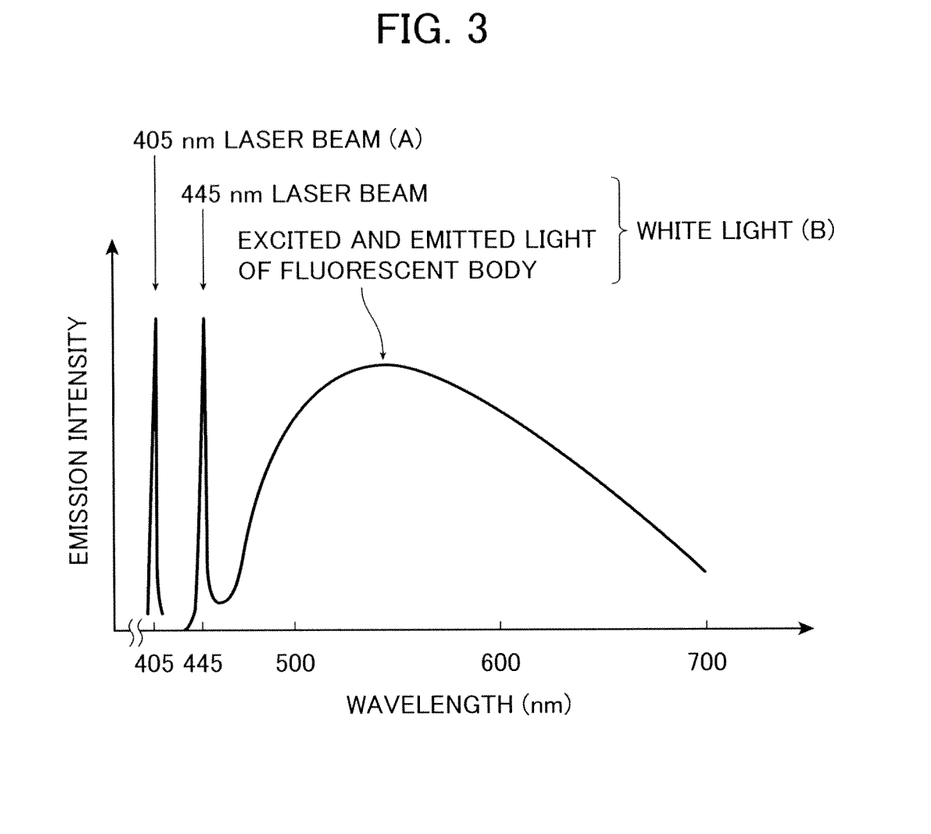
FIG. 3 is a graph showing emission spectra of a blue-violet laser seam (a 405 nm laser beam (A)) that is used for a light source device of the endoscope apparatus shown in FIG. 2 and is emitted from a blue-violet laser beam source, and emission spectra of white light (B) that is emitted from a unite light source including a blue laser bean source and a fluorescent body.

FIG. 3 is a graph showing emission spectra of a blue-violet laser beam from the 405LD 34, and emission spectra of a blue laser beam from the 445LD 32 and a fluorescent light when the wavelength of a blue laser beam is converged by the fluorescent body 24. The blue-violet laser bean is expressed by an emission line (profile A) with a central wavelength of 405 nm, is the narrowband light of the invention, and is used mainly as special light (in the case of special light mixed with the white light, the special light constitutes a portion of the white light). Additionally, the blue laser bean is expressed by an emission line with a central wavelength of 445 nm, and excited and emitted light from the fluorescent body 24 caused by the blue laser beam has spectrum intensity distribution in which emission intensity increases in a wavelength band of approximately 450 nm to 700 nm. The above-described white light is formed by a profile B by the excited and emitted light and the blue laser beam, and is used mainly as normal light.

Here, the white light in the invention is not strictly limited to that including all the wavelength components of visible light and, for example, may include the light of a specific wavelength band, such as R, G, and B, including the above-described pseudo-white light. For example, the white light broadly includes the light including wavelength components from green to red, the light including wavelength components from blue to green, or the like.

In the endoscope apparatus 10, the emission intensities of the profile A and the profile B can be controlled so as to be relatively increased and decreased by the light source control section 48, to produce irradiation light with arbitrary luminance balance. In addition, in the endoscope apparatus 10 of the invention, in the normal light mode, only the light of the profile B is used and the light of superimposed profiles A and B is used in the special light mode.

As described above, illumination light including the white light (profile B) based on the blue laser beam from the 445LD 32 and the excited and emitted light from the fluorescent body 24, and the narrowband light (profile A) based on the blue-violet laser beam from the 405LD 34 is emitted from the irradiation port 28A of the distal end portion of the endoscope 12 toward the region to be observed of a subject. The return light from a region to be observed that is irradiated with the illumination light is focused on the light-receiving surface of the imaging element 26 via the light-receiving part 28B, and the region to be observed is captured by the imaging element 26.

An image signal (captured image signal) of a captured image output from the imaging element 26 after the imaging is input to an image processing system 36 of the processor 16 through a scope cable 30.

Next, the image signal of the captured image captured and output by the imaging element 26 in this way is subjected to image processing in a signal processing system including the image processing system 36 of the processor 16, is output to a monitor 38 or a recording device 42, and is provided for observation by the user.

Additionally, signal processing systems of respective sections including the detailed configuration of a processor of a first embodiment of the endoscope apparatus of the invention shown in FIG. 2 will be described in detail.

As shown in this drawing, the signal processing system of the endoscope apparatus 10 has a signal processing system of the endoscope 12, a signal processing system of the light source device 14, a signal processing system (image processing system 36) of the processor 16, and the monitor 38, input section (mode switching section) 40 and recording device 42 of the input and output section 18.

The signal processing system of the endoscope 12 is a signal processing system for captured image signals from the imaging element 26, and has a CDS and AGC circuit 44 for performing correlated double sampling (CDS) or automatic gain control (AGC) on the captured image signals that are analog signals, and an A/D converter (A/D converter) 46 that converts analog image signals subjected to sampling and gain control in the CDS and AGC circuit 44 into digital image signals. The digital image signals that are A/D converted in the A/D converter 46 are input to the image processing system 36 of the processor 16 via a connector part.

Additionally, the signal processing system of the light source device 14 has a light source control section 48 that performs ON/OFF control and light quantity control of the 445LD 32 and the 405LD 34.

Here, the light source control section 49 turns on the 445LD 32 and the 405LD 34 according to a light source ON signal accompanying the operation start of the endoscope apparatus 10, and performs the ON/OFF control of the 405LD 34 according to the switching signal between the normal light mode and the special light mode from the mode switching section 40.

Additionally, the light source control section 48 controls the emission light quantity of the 445LD 32 and the 405LD 34, that is, the irradiation light quantity of the illumination light from the light source device 14 by changing the emission intensities of the 445LD 32 and the 405LD 34, that is, the values of electric currents passed to the light sources 32 and 34, according to the light quantity of B light, G light, and R light based on a captured image signal calculated from a light quantity calculating section 50 to be described below, the emission intensities of the profile A and the profile B, or the like.

Additionally, in principle, the light quantity of return light is calculated, for example, using a captured image signal of a predetermined portion (predetermined pixel) in a captured image in the light quantity calculating section 50 to be described below such chat an irradiation light quantity suitable for imaging is obtained, and the light source control section 46 controls the light sources 32 and 34 such that the light quantity of the return light fails within a predetermined range. That is, the light quantity calculating section 50 to be described below calculates information on automatic exposure in order to control the light source control section 43, and the automatic exposure (AE) is performed by the light quantity calculating section 50 and the light source control section 48.

In addition, here, the information on the automatic exposure is a parameter for automatically determining the exposure during imaging, and is determined on the basis of the light quantity of the return tight of the predetermined portion of the captured image detected by the imaging element 26. Even in moving image imaging, the information on the automatic exposure is determined by the light quantity of the return light in the imaging time per frame that is settled according to the storage time (storage time of CCD or CMOS corresponding to an RGB color filter) of the imaging element 26.

Moreover, the signal processing system of the processor 16 is the image processing system 36 (refer to FIG. 1), and has a light quantity calculating section 50, a DSP (digital signal processor) 52, a denoising circuit 54, a density calculating section 55, an image processing switching section 60, an image processing section 62, and an image display signal generating section 66.

The light quantity calculating section 50 calculates the light quantity of return light received in the imaging element (sensor) 26, as mentioned above, using captured image signals input via a connector from the A/D converter 46 of the endoscope 12.

Additionally, the light quantity calculating section 50 calculates light source light quantities, that is, the light quantity (emission intensity) of the blue laser beam from the 445LD 32, the light quantity (spectrum intensity distribution shown by excited and emitted light) of the white light from the fluorescent body 24 based on this blue laser beam, and the light quantity (emission intensity of the blue-violet laser beam from the 405LD 34, and the like, through the light source control section 48, and calculates the light quantity ratio (light emission ratio of 405LD/445LD) between the irradiation light quantity of the illumination light directed to a subject from the light source device 14, and the 445LD 32 and the 405LD 34 from these light quantities.

The light quantity calculating section 5C controls the light source control section 48, using the light quantity of the return light and the irradiation light quantity that are calculated as mentioned above, as the aforementioned information on automatic exposure, and adjusts the white balance gain of the CDS/AGC circuit 44 from the light quantity ratio if required.

The DSP 52 performs gamma correction and color correction processing on the digital image signals output from the A/D converter 46 after the irradiation light quantity and the light quantity of the return light is detected by the light quantity calculating section 50.

The denoising circuit 54 implements a denoising method in image processing, such as a moving-average method or a median filter method, and removes noise from the digital image signals subjected to the gamma correction and color correction processing in the DSP 52.

The digital image signals input to the processor 16 from the endoscope 12 in this way are subjected to preprocessing, such as gamma correction, color correction processing, and denoising, in the DSP 52 and the denoising circuit 54.

Figure 4:
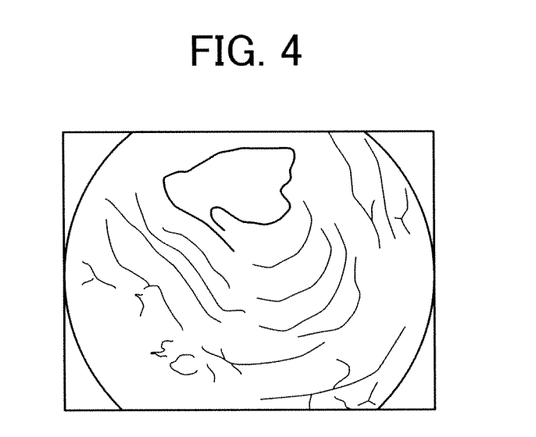
FIG. 4 shows an example of a captured image that is observed when the endoscope is inserted into and extracted from an alimentary canal, in the endoscope apparatus of the invention.

Next, the density calculating section 55 calculates the density of each pixel of the captured image from the captured image signals that are denoised in the denoising circuit 54. Specifically, for example, the density calculating section calculates the intensities of an R light image signal, a G light image signal, and a B light image signal in each pixel from the captured image shown in FIG. 4, and sums up these intensities, thereby adopting the resulting value as the density of each pixel.

The density calculating section 55 outputs the density of each pixel of the captured image to a structure enhancing section 74 of the image processing section 62 to be described below as density information.

The image processing switching section 60 is a switch that switches whether the preprocessed digital image signals are sent to the color converter 68 of the image processing section 62 in the subsequent stage or are sent to the special light color conversion section 70 of the image processing section 62, or the basis of the instruction (switching signal) of the node switching section 40 to be described below.

In addition, in the invention, for the purpose of distinction, digital image signals before image processing using the image processing section 62 are referred to as image signals, and digital image signals before and after image processing are referred to as image data.

The image processing section 62 is a section that performs image processing suitable for preprocessed digital image signals using the blue-violet laser beam (profile A) from the 405LD 34, and the white light (profile B) from the 445LD 32 and the fluorescent body 24, and has the color converter 68, the special light color conversion section 70, the color enhancing section 72, and the structure enhancing section 74.

The color converter 68 performs color conversion processing, such as matrix processing of 3×3, grayscale conversion processing, and three-dimensional LUT processing, on preprocessed RGB 3-channel digital image signals, and converts image signals into color-conversion-processed RGB image data.

The special light color conversion section 70 multiplies a G image signal of digital image signals of input preprocessed RGB3 channels by a predetermined coefficient to allocate the resulting value to R image data, and multiplies a B image signal by a predetermined coefficient to allocate the resulting values to G image data and B image data, respectively, thereby generating RGB image data, and then performs color conversion processing, such as 3×3 matrix processing, grayscale conversion processing, and three-dimensional LUT processing, on the generated RGB image data similarly to the color converter 68.

The color enhancing section 72 is provided to give a difference in chroma between a blood vessel and a membrane in a screen, to enhance the blood vessel so that the blood vessel is clearly visible. For example, the average value of the chroma of the overall screen is checked with respect to the color-conversion-processed RGB image data, and enhancement processing is performed in a direction in which a difference is given to the chroma between the blood vessel and the membrane from the average value of the chroma.

The structure enhancing section 74 performs structure enhancement processing, such as sharpness or contour enhancement, on the color-enhanced RGB image data.

Additionally, the structure enhancing section 74 includes a frequency band enhancing section 76, and performs frequency band enhancement processing on the color-enhanced RGB image data in the frequency band enhancing section 76, on the basis of the density information of each pixel of the captured image from the aforementioned density calculating section 55, as a kind of the aforementioned structure enhancement processing.

The frequency enhancement processing of the frequency band enhancing section 76 is performed by applying a predetermined frequency band filter to captured image data. By applying different frequency band filters according to the density of each pixel, better enhancement can be made so that a captured image corresponds to a purpose.

Additionally, a plurality of captured images obtained applying the different frequency band filters may be created, and the plurality of captured images may be synthesized according to the density of each pixel.

Figure 5A:
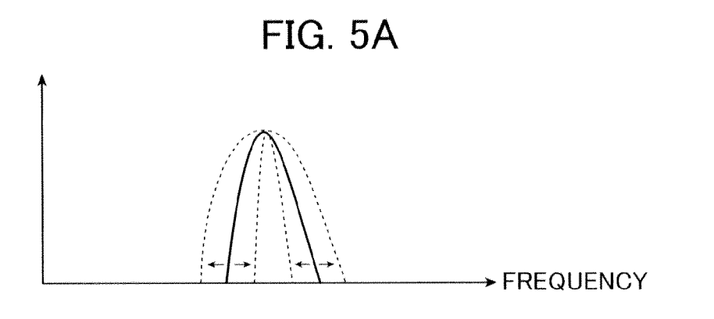
FIG. 5A shows an example of changes of a frequency band filter when bandwidth is changed according to density or the like, FIG. 5B shows an example of changes of the frequency band filter when a central frequency is changed according to density or the like, FIG. 5C shows an example of changes of the frequency band filter when an enhanced frequency is changed according to density or the like, and FIG. 5D shows an example of changes of the frequency band filter in which one side is open.

A frequency band filter to apply may increase the bandwidth of a filter according to pixel density, for example, as shown in FIG. 5A. For example, when the density is thick (dark), the bandwidth may be made wide, and when the density is thin (bright), the bandwidth may be made narrow.

Figure 5B:
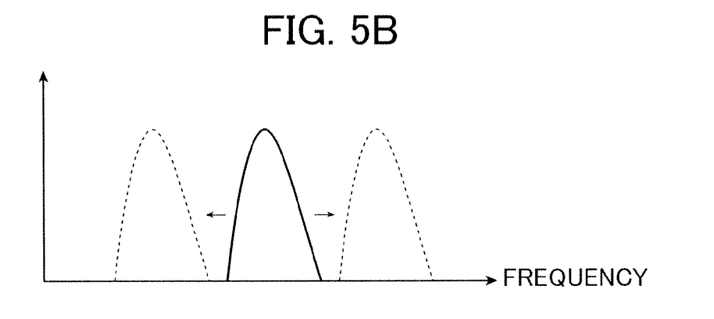

Additionally, as shown in FIG. 5B, the central frequency of a filter may be changed, according to pixel density. For example, when the density is thick, the central frequency may be made high, and when the density is thin, the central frequency may be made narrow.

Figure 5C:
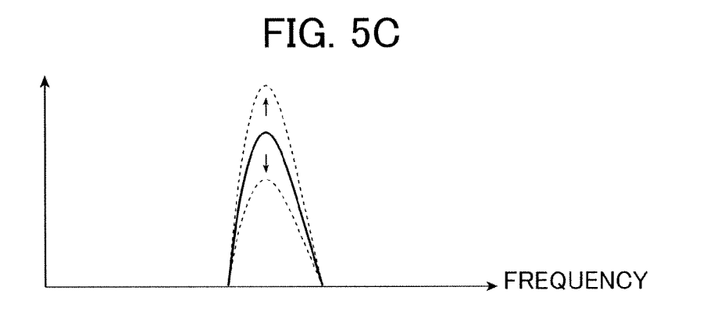

Moreover, as shown in FIG. 5C, the enhancement degree of a filter may be changed according to pixel density. For example, when the density is thick, the enhancement degree of a frequency enhancing filter may be weakened, and when the density is thin, the enhancement degree of the frequency enhancing filter may be strengthened.

The bandwidth, the central frequency, and the enhancement degree may be gradually changed or may be continuously changed according to the density.

Additionally, these may be combined and changed. For example, when the density is thick, the bandwidth may be made wide, the central frequency may be made high, the enhancement degree may be made weak, and when the density is thin, the bandwidth may be made narrow, the central frequency may be made low, and the enhancement degree may be made strong.

Figure 5D:
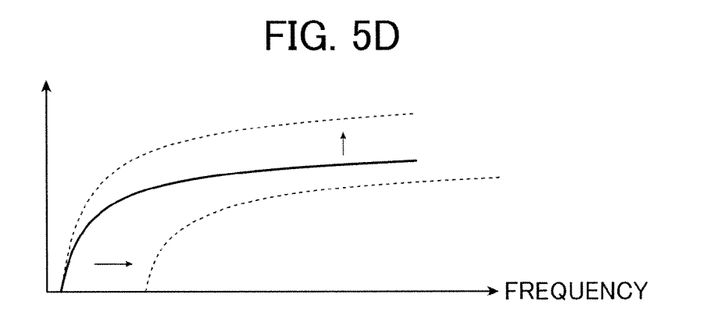

Additionally, as shown in FIG. 5D, the frequency band filter may have one side open. Even in the filter of FIG. 5D, similarly to the aforementioned FIGS. 5A to 5C, the enhancement degree may be changed or the frequency band may be moved.

In addition, the determination of low density, middle density, and high density with thin or thick density may be determined, for example, on the basis of the average value of pixel densities of the overall captured image, and the reference value of pixel densities may be provided in advance apart from the average value.

As a specific example to which the frequency band filter is applied, in a captured image, it is considered that, in a region where the pixel density is a relatively low density, the distance between the distal end of the endoscope and a subject is sufficiently short, and enlarged observation is performed. Therefore, surface layer fine blood vessels can be assumed as a target to be captured, and a frequency band filter that can enhance a high-frequency portion is applied to the aforementioned RGB image data sc that the fine structure of the surface layer fine blood vessels can be individually separated as fine lines.

Additionally, for example, in a captured image, it is considered that, in a region where the pixel density is middle density, the distal end of the endoscope is slightly apart from a subject, and near-distance observation that requires a greater or smaller light quantity than that in the aforementioned enlarged observation is performed. Therefore, each of fine blood vessels slightly larger than the fine structure of surface layer fine blood vessels as a target to be captured can be assumed as a target to be captured, and a frequency enhancing filter that can enhance a middle-frequency portion is applied to the aforementioned RGB image data so that the atmosphere of the surface layer fine blood vessels can be enhanced.

Moreover, in a captured image, it is considered that, in a region where the pixel density is high density, the distal end of the endoscope is apart from a subject, and tar-distance observation that requires a larger quantity of light is performed. Therefore, a region called a brownish region where surface layer fine blood vessels are densely present as a lump rather than individual surface layer fine blood vessel can be assumed as a target to be captured.

The region called a brownish region is assumed to be a region in an early-stage cancer, and many such regions have a size of about 1 mm, but some have a size of 2 mm or 3 mm. If a frequency band filter with narrow bandwidth, for example, is used, in order to enhance this frequency band, brownish regions outside the frequency band of this filter, even if only slightly outside, will not enhanced at all.

Hence, in order to enhance all brownish regions with various sizes, it is desirable to use a frequency band filter in which the bandwidth is large or one side is great-y open.

In the frequency band enhancing section 76 of the structure enhancing section 74, the RGB image data that has been subjected to optimal frequency enhancement processing is input to the image display signal generating section 66 from the image processing section 62 as image-processed RGB image data, on the basis of the aforementioned density information for each pixel.

The image display signal generating section 66 converts the image-processed RGB image data input from the image processing section 62 into display image signals for being displayed as a soft copy image in the monitor 38 or for being output as a hard copy image in the recording device 42.

The monitor 38 displays, as a soft copy image, a normal light observation image based on display image signals that are obtained in the imaging element 26 by the irradiation of white light and subjected to the preprocessing and the normal light image processing in the processor 16, in the normal light mode, and displays, as a soft copy image, a special light observation image based on display image signals that are obtained in the imaging element 26 by the irradiation of special light in addition to white light and subjected to the preprocessing and the special light image processing in the processor 16, in the special light mode.

Figure 6:
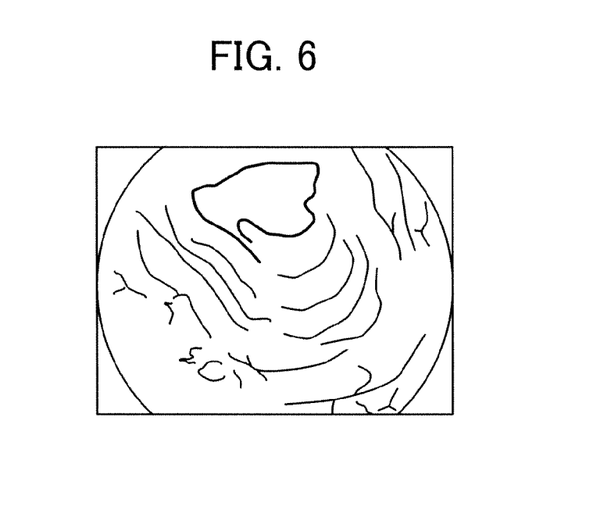
FIG. 6 is an example of a captured image when the frequency band filter is applied to the captured image shown in FIG. 4.

A captured image as shown in FIG. 6 to which a frequency band filter is applied according to pixel density that is subjected to the structure enhancement processing corresponding to a purpose is displayed on the monitor 38.

The recording device 42 also outputs the normal light observation image obtained by the irradiation of white light as a hard copy image in the normal light mode, and outputs the special light observation image obtained by the irradiation of white light and special light as a hard copy image in the special light mode.

In addition, if required, the display image signals generated in the image display signal generating section 66 may be recorded as image information in the recording device 42 including a memory or a storage device, though not shown.

On the other hand, the mode switching section 40 has mode switching buttons for performing switching between the normal light mode and the special light mode, and a mode switching signal from the mode switching section 40 is input to the light source control section 48 of the light source device 14. Here, although the mode switching section 40 is arranged as the input section 40 of the input/output section 18, the mode switching section may be arranged at the processor 16, the manipulation part of the endoscope 12, or the light source device 14. In addition, a switching signal from the mode switching section 40 is output to the light source control section 48 and the image processing switching section 60.

The first embodiment of the endoscope apparatus of the invention is basically configured as described above.

The operation of the first embodiment of the endoscope apparatus of the invention will be described below with reference to the flowchart of FIGS. 7 and 8.

The invention does not place restrictions on the normal light observation or the special light observation. Hence, for example, description will be made taking the case where the special light observation is performed as an example.

In the present embodiment, first, normal light observation shall be performed in the normal light node. That is, the 445LD 32 is turned on, and normal light image processing is performed on captured image data based on white light in the image processing section 62.

Here, switching to the special light mode is performed by a user. A mode switching signal (special light ON) is output as the user manipulates the mode switching section 40, and the image processing is switched to the special light mode in the image processing switching section 6C.

Next, a mode switching signal is also input to the light source control section 48 of the light source device 14, the 405LD 34 is turned on by the light source control section 43, and illumination light in which white light and narrowband light are mixed is emitted to a subject (S10).

The illumination light is reflected by the subject, and the return light thereof is acquired as captured image signals by the imaging element 26 (S12).

Next, the captured image signals acquired by the imaging element 26 have a white balance gain adjusted and are converted into digital data, and are then sent to the light quantity calculating section 50. In the light quantity calculating section 50, the light quantity of the return light is calculated on the basis of the captured image signals of a predetermined portion of the captured image (S14).

When the light quantity of the return light calculated in the light quantity calculating section 50 is not within a predetermined range that is required for imaging, an instruction is issued to the light source control section 49 from the light quantity calculating section 50, and adjustment of the irradiation light quantity is performed by the light source control section 48 (S16). When the light quantity of the return light is insufficient, an instruction of raising the irradiation light quantity is issued to the light source control section 48, and when the light quantity of the return light is excessively large, an instruction of lowering the irradiation light quantity is issued to the light source control section 48.

In addition, the light quantity calculating section 50 also acquires information on the irradiation light quantity of the light source device 14, that is, information on the emission light quantity of the 445LD 32 and the 405LD 34 and the light quantity ratio thereof, from the light source control section 48. Additionally, the white balance gain of the CDS/AGC circuit 44 may be adjusted from the aforementioned information on the emission light quantity and the light quantity ratio, and the light quantity of the return light.

After the adjustment of the irradiation light quantity is performed, captured image signals are again acquired by the imaging element 26 (S18).

If the captured image signals are acquired again, the density calculating section 55 calculates the density of each pixel from an RGB image based on the captured image signals. The information on the density of each pixel calculated is output to the frequency band enhancing section 76 of the structure enhancing section 74 of the image processing section 62 (S20).

Then, image processing of the captured image data is changed on the basis of the density of each pixel calculated in the density calculating section 55. The change of the image processing is performed by changing frequency processing conditions applied to the captured image data in the structure enhancing section 74 of the image processing section 62.

Specifically, in the frequency band enhancing section 76 of the structure enhancing section 74, a frequency band filter is set for each pixel according to the density of each pixel of the aforementioned captured image (S22).

The captured image data obtained in endoscope observation is output to the image processing section 62, is subjected to the aforementioned image processing through the color converter 68 or the special light color conversion section 70, and the color enhancing section 72, and is input to the structure enhancing section 74. A frequency band filter that is set for each pixel as mentioned above is applied to the captured image data input to the structure enhancing section 74, in the frequency band enhancing section 76 (S24).

In the image processing section 62, a frequency enhancing filter according to the density of each pixel is applied, and the image-processed captured image data is output to the image display signal generating section 66. The image display signal generating section 66 generates and outputs image display signals from this image information.

The output image display signals are displayed on the monitor 38 as an endoscope observation image, and are recorded by the recording device 42 (S261.

From the above, a captured image subjected to suitable frequency processing according to the density of each pixel can be displayed.

The above is the operation of the first embodiment of the endoscope apparatus of the invention.

Next, a second embodiment of the endoscope apparatus of the invention will be described focusing on differences from the first embodiment.

The difference between the second embodiment of the endoscope apparatus of the invention and the first embodiment is that, when an enhanced frequency in image processing is set, the light quantity information (including the irradiation light quantity of illumination light, the light quantity of return light, the light quantity ratio thereof when there is a plurality of light sources, and the aforementioned information on automatic exposure) is calculated in the light quantity calculating section 50 as well as the density information (the density of each pixel of a captured image), and the enhanced frequency is set by taking the light quantity information into consideration along with the density information.

Figure 9:
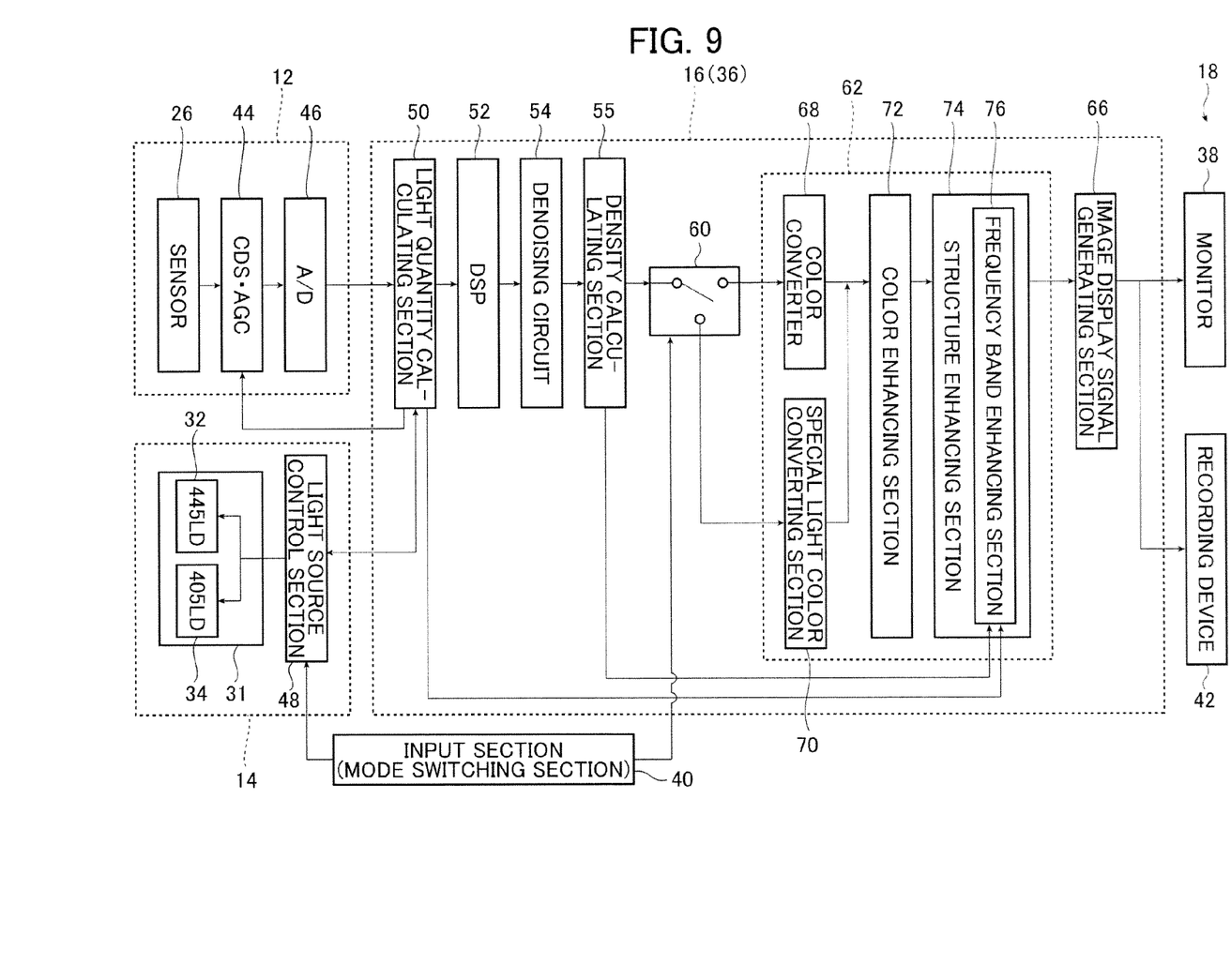
FIG. 9 is a block diagram showing signal processing systems of respective sections including the detailed configuration of a second embodiment of the endoscope apparatus shown in FIG. 1.

Hence, the difference in apparatus configuration between the second embodiment, and the first embodiment of the endoscope apparatus is that, as shown in FIG. 9, the light quantity information in captured image signals is output to the structure enhancing section 74 from the light quantity calculating section 50 along with the density information of each pixel from the aforementioned density calculating section 55.

In the frequency band enhancing section 76 of the structure enhancing section 74, setting of a frequency band filter is performed more precisely than the first embodiment, on the basis of the light quantity information from the light quantity calculating section 50 and the density information from the density calculating section 55.

If the color of a subject is not taken into consideration, it is believed that the product of the "light quantity information" and the "density information (pixel value)" is proportional to the distance of each pixel of a captured image. Therefore, the setting of a frequency band filter that is more suitable than the first embodiment can be performed, and a captured image subjected to more suitable frequency processing can be obtained.

The above are configurational differences between the first embodiment and the second embodiment of the invention.

Additionally, the operation of the second embodiment of the endoscope apparatus of the invention will also be described focusing on the differences from the first embodiment.

Figure 7:
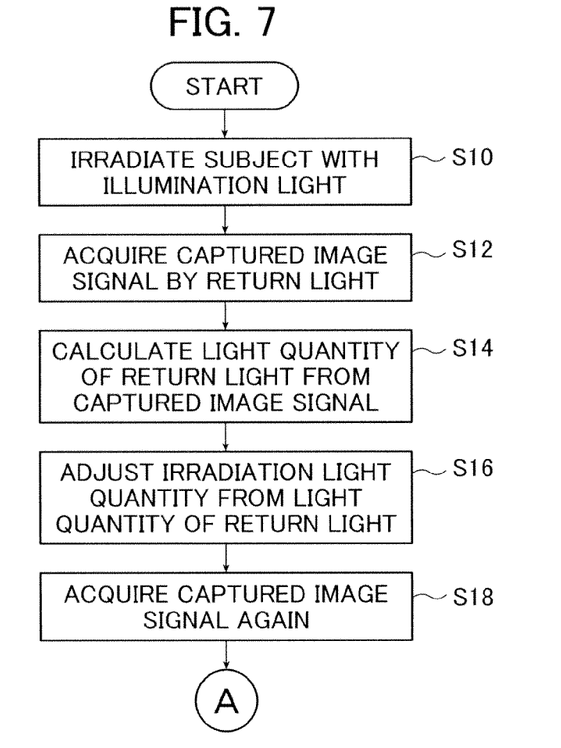
FIG. 7 is a flowchart showing one example of a flow until the irradiation light quantity is adjusted and a captured image signal is acquired again, in the endoscope observation carried out by the endoscope apparatus shown in FIG. 1.

The operation of the second embodiment of the invention is the same regarding the steps shown in FIG. 7. The second embodiment implements the steps shown in FIG. 10 instead of the steps shown in FIG. 9.

Figure 8:
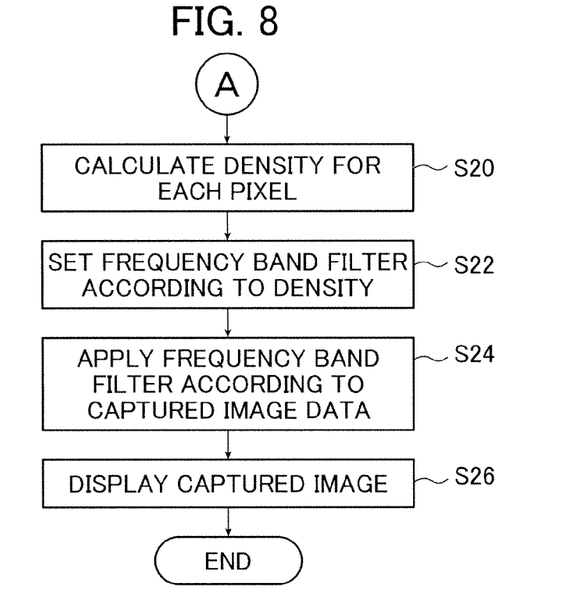
FIG. 8 is a flowchart showing one example of a flow after a captured image signal is acquired again, in the endoscope observation in the first embodiment of the endoscope apparatus shown in FIG. 1.
Figure 10:
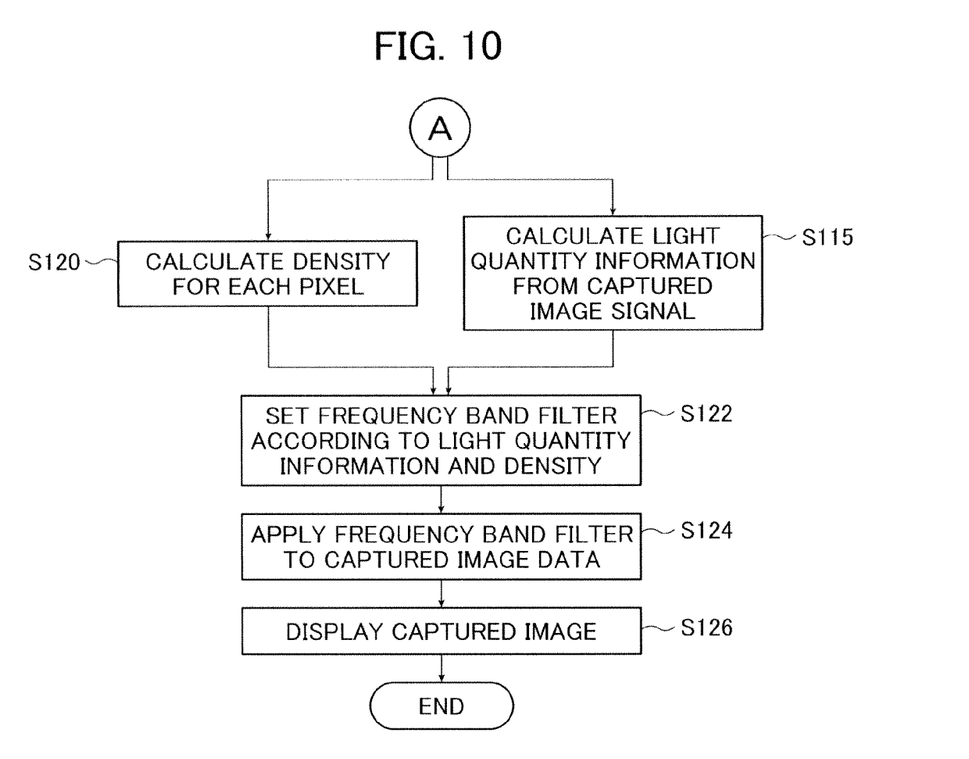
FIG. 10 is a flowchart showing one example of a flow after a captured image signal is acquired again, in the endoscope observation in the second embodiment of the endoscope apparatus shown in FIG. 1.

In FIG. 10, since Step S120 is the same as Step S20 of FIG. 8, the description thereof is omitted.

Additionally, in the invention, as mentioned above, the light quantity calculating section 50 calculates the light quantity of return light from captured image signals, and the irradiation light quantity of illumination light (including the light quantity ratio when there is a plurality of light sources) from the light source control section 48, respectively, as the light quantity information (S115).

Next, the light quantity information of a captured image is acquired from the light quantity calculating section 50, the density information of the captured image is acquired from the density calculating section 55, and a frequency band filter is set on the basis of the density information and the light quantity information in the frequency band enhancing section 76 (S122). A more suitable enhanced frequency can be set as compared to the first embodiment in which the setting of the enhanced frequency is performed only with the density information.

In addition, since Step S124 and Step S126 are the same as Step S24 and Step S26 of FIG. 8, the description thereof is omitted.

Thereby, a captured image subjected to suitable frequency processing according to the light quantity information and density information of the captured image can be displayed.

The above is the second embodiment of the endoscope apparatus of the invention.

Next, a third embodiment of the endoscope apparatus of the invention will be described focusing on differences from the second embodiment.

The difference between the third embodiment of the endoscope apparatus of the invention and the second embodiment is that, when a frequency band filter in image processing is set, the distance of each pixel is estimated from the density information and the light quantity information, and a frequency band filter is set according to the distance of each pixel.

Figure 11:
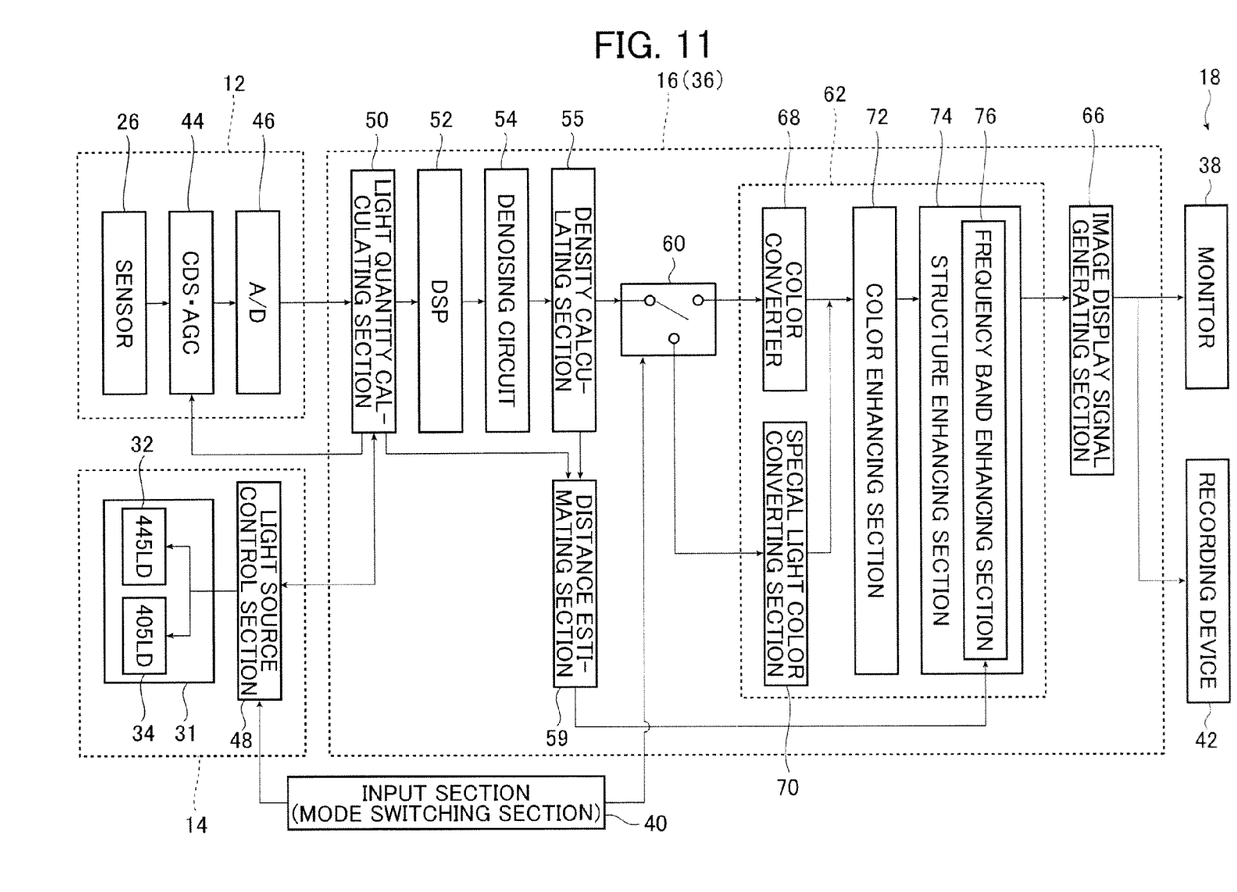
FIG. 11 is a block diagram showing signal processing systems of respective sections including the detailed configuration of a third embodiment of the endoscope apparatus shown in FIG. 1.

Hence, the difference in apparatus configuration between the third embodiment and the second embodiment of the endoscope apparatus, as shown in FIG. 11, is that a distance estimating section S9 is included, light quantity information is output to the distance estimating section 59 from the light quantity calculating section 50 along with the density information of each pixel from the aforementioned density calculating section 55, the distance of each pixel is estimated from the light quantity information and the density information in the distance estimating section 59. The information on the estimated distance of each pixel is output to the frequency band enhancing section 76 of the structure enhancing section 74, and a frequency band filter is set according to the distance of each pixel in the frequency band enhancing section 76.

Here, the distance of each pixel means the distance from the distal end of the endoscope to a subject portion corresponding to each pixel.

As for estimation of the distance of each pixel in the distance estimating section 59, first, the distance to a predetermined pixel (predetermined portion) in a captured image is first estimated using light quantity information. Here, the light quantity information is the light quantity of the return light of a predetermined portion in a captured image signal that is the control information of AE, and is information including the ratio of the irradiation light quantity of illumination light, and the light quantity of return light. Since no light sources other than the illumination light that the endoscope itself irradiates are present in the endoscope observation, the distance to a subject (predetermined portion) can be estimated from the irradiation light quantity of illumination light and the light quantity of return light.

Next, in a captured image, the density difference between a predetermined pixel whose distance is estimated, and other pixels is calculated according to the density of each pixel mentioned above. The distance of each pixel can be estimated with a predetermined pixel as a reference, on the basis of the density difference between a predetermined pixel and other pixels.

The distance of each pixel estimated in the distance estimating section 59 is output to the frequency band enhancing section 76 of the structure enhancing section 74.

In the frequency band enhancing section 76 of the structure enhancing section 74, a frequency band filter is set according to the estimated distance of each pixel.

Although the setting of a frequency band filter is the same as that of the first embodiment and the second embodiment, a higher-precision frequency band filter can be set. The above are the configurational differences of the third embodiment of the endoscope apparatus.

Additionally, the operation of the third embodiment of the endoscope apparatus of the invention will also be described focusing on the differences from the second embodiment.

The operation of the third embodiment of the invention is the same regarding the steps shown in FIG. 7. The third embodiment takes the steps shown in FIG. 12 instead of the steps shown in FIG. 10 of the second embodiment.

Figure 12:
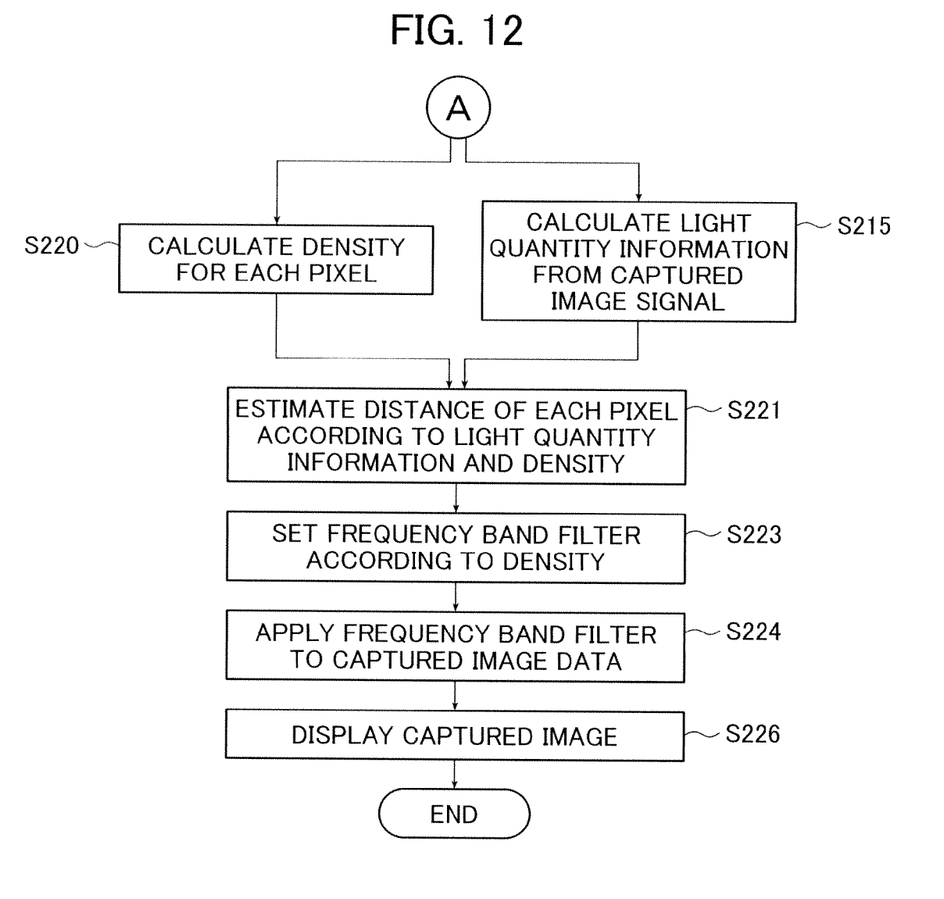
FIG. 12 is a flowchart showing one example of a flow after a captured image signal is acquired again, in the endoscope observation in the third embodiment of the endoscope apparatus shown in FIG. 1.

In FIG. 12, Steps S215, S220, S224, and S226 are the same as Steps S115, S120, S124, and S126 of FIG. 10. Hence, the description thereof is omitted. The differences between the third embodiment and the second embodiment are Step S122, Step S221 and Step S223.

In the invention, as mentioned above, first, the aforementioned light quantity information is acquired from the light quantity calculating section 50, the density information of a captured image is acquired from the density calculating section 55, and the distance of each pixel in the captured image is estimated on the basis of the density information and the light quantity information in the distance estimating section 59 (S221).

The distance of each pixel estimated in the distance estimating section 59 is output to the structure enhancing section 74, and a frequency band filter is set on the basis of the distance of each estimated pixel in the frequency band enhancing section 76 of the structure enhancing section 74 (S223). By estimating the distance of each pixel and setting a frequency band filter according to distance, a higher-precision frequency band filter can be set as compared to the first embodiment and the second embodiment.

The above is the endoscope apparatus related to the third embodiment of the invention.

Figure 13:
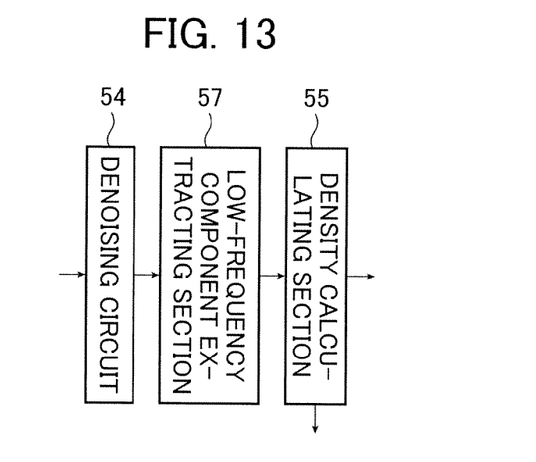
FIG. 13 is a drawing of an extracted part when the block diagrams showing in FIGS. 2, 9, and 11 include a low-frequency component extracting section.

In addition, as shown in FIG. 13, in the first to third embodiments, a low-frequency component extracting section 57 that extracts the low-frequency component of a captured image signal may be provided before the density calculating section 55, and the density information of each pixel of a captured image may be calculated on the basis of a low-frequency image signal extracted by the low-frequency component extracting section 57. By extracting the low-frequency component to create an image, a captured image in which a blood vessel portion is enhanced can be obtained.

Although the endoscope apparatus of the invention has been described in detail above, the invention is not limited to the above embodiments, and various improvements and modifications may be performed without departing from the scope of the invention.

What is claimed is:

1. An endoscope apparatus comprising:
a light source unit that is capable of adjusting quantity of light and irradiates illumination light to a subject;
an imaging element that captures a captured image by return light from a living body that is the subject in the illumination light and outputs a captured image signal;
a brightness calculating section that calculates a value of brightness of each pixel of the captured image on basis of the captured image signal; and
an image processing section that performs a predetermined image processing on the captured image,
wherein the light source unit includes:
a first light source section that emits broadband light having a wide wavelength band including a visible region,
a second light source section that emits narrowband light having a wavelength bandwidth narrowbanded according to spectral characteristics of the structure and components of the living body used as the subject, and
a light source control section that controls light emission, irradiation light quantity, and a light quantity ratio from the first light source section and the second light source section,
wherein the image processing section includes a frequency band enhancing section that applies a predetermined frequency band filter to the captured image, and
wherein the frequency band enhancing section determines whether a value of brightness of a particular region of the captured image is either larger or smaller than an average value of the brightness of pixels of the captured image or a reference value provided in advance, whereby when the value of brightness of the particular region is larger than the average value or the reference value, an enhancement degree of the frequency band filter is strengthened, and when the value of brightness of the particular region is smaller than the average value or the reference value, the enhancement degree of the frequency enhancing filter is weakened.

2. The endoscope apparatus according to claim 1, wherein the frequency band enhancing section strengthens the enhancement degree as the value of brightness becomes large, and weakens the enhancement degree as the value of brightness becomes small.

3. The endoscope apparatus according to claim 1, wherein the frequency band enhancing section narrows bandwidth of a frequency band to be enhanced when the value of brightness of the particular region is larger than the average value or the reference value, and increases the bandwidth of the frequency band to be enhanced when the value of brightness of the particular region is smaller than the average value or the reference value.

4. The endoscope apparatus according to claim 1, wherein the frequency band enhancing section lowers a center of a frequency band to be enhanced when the value of brightness of the particular region is larger than the average value or the reference value, and raises the center of the frequency band to be enhanced when the value of brightness of the particular region is smaller than the average value of the reference value.

5. The endoscope apparatus according to claim 1, further comprising a low-frequency component extracting section that extracts a low-frequency component of the captured image from the captured image signal to generate a low-frequency captured image, and outputs a low-frequency captured image signal,
wherein the low-frequency captured image signal is used instead of the captured image signal in the brightness calculating section.

\* \* \* \* \*